United States Patent
Hu et al.

(10) Patent No.: US 9,782,366 B2
(45) Date of Patent: Oct. 10, 2017

(54) DRUG FOR KILLING ACID-FAST (RED) BACILLUS

(71) Applicant: Shuxian Hu, Shenyang (CN)

(72) Inventors: Shuxian Hu, Shenyang (CN); Xiaoli Wang, St. Louis, MO (US); Liyuan Cao, Markham (CA); Kai Jiao, Shenyang (CN); Hong Zhang, Shenyang (CN)

( * ) Notice: Subject to any disclaimer, the term of this patent is extended or adjusted under 35 U.S.C. 154(b) by 0 days.

(21) Appl. No.: 14/760,458

(22) PCT Filed: Nov. 15, 2013

(86) PCT No.: PCT/CN2013/001393
§ 371 (c)(1),
(2) Date: Jul. 10, 2015

(87) PCT Pub. No.: WO2014/107828
PCT Pub. Date: Jul. 17, 2014

(65) Prior Publication Data
US 2015/0352063 A1    Dec. 10, 2015

(30) Foreign Application Priority Data

Jan. 11, 2013  (CN) .......................... 2013 1 0011373
May 14, 2013  (CN) .......................... 2013 1 0177413

(51) Int. Cl.
| | | |
|---|---|---|
| *A61K 31/15* | (2006.01) | |
| *A61K 9/48* | (2006.01) | |
| *A61K 9/08* | (2006.01) | |
| *A61K 31/136* | (2006.01) | |
| *A61K 9/00* | (2006.01) | |
| *A23L 5/42* | (2016.01) | |
| *A23L 33/10* | (2016.01) | |

(52) U.S. Cl.
CPC ................ *A61K 31/15* (2013.01); *A23L 5/42* (2016.08); *A23L 33/10* (2016.08); *A61K 9/0014* (2013.01); *A61K 9/0053* (2013.01); *A61K 9/08* (2013.01); *A61K 9/4875* (2013.01); *A61K 31/136* (2013.01); *A23V 2200/00* (2013.01)

(58) Field of Classification Search
None
See application file for complete search history.

(56) References Cited

PUBLICATIONS

Conn HJ. "A Report on Basic Fuchsin". Science. Oct. 24, 1924; 60(1556):387-388.*
Selvakumar et al. "Comparison of Variants of Carbol-Fuchsin Solution in Ziehl-Neelsen for Detection of Acid-Fast Bacilli". Int J Tuberc Lung Dis. 2005; 9(2):226-229.*
Wagenaar M. "The Detection of Rice Flour in Other Flours and in Spices". Pharmaceutisch Weekblad. 1928; 65:246-251. [Abstract Only].*
Sabnis RW. Handbook of Biological Dyes and Stains. Wiley Publishing. 2010.*

* cited by examiner

*Primary Examiner* — Leslie A. Royds Draper
(74) *Attorney, Agent, or Firm* — Tsz Lung Yeung

(57) ABSTRACT

Disclosed is a drug for killing acid-fast (red) *bacillus* and use thereof. The drug, using fuchsin as active ingredient, can effectively kill acid-fast *bacillus* and remove *mycobacterium tuberculosis* and leprosy *bacillus* in human body.

2 Claims, 1 Drawing Sheet

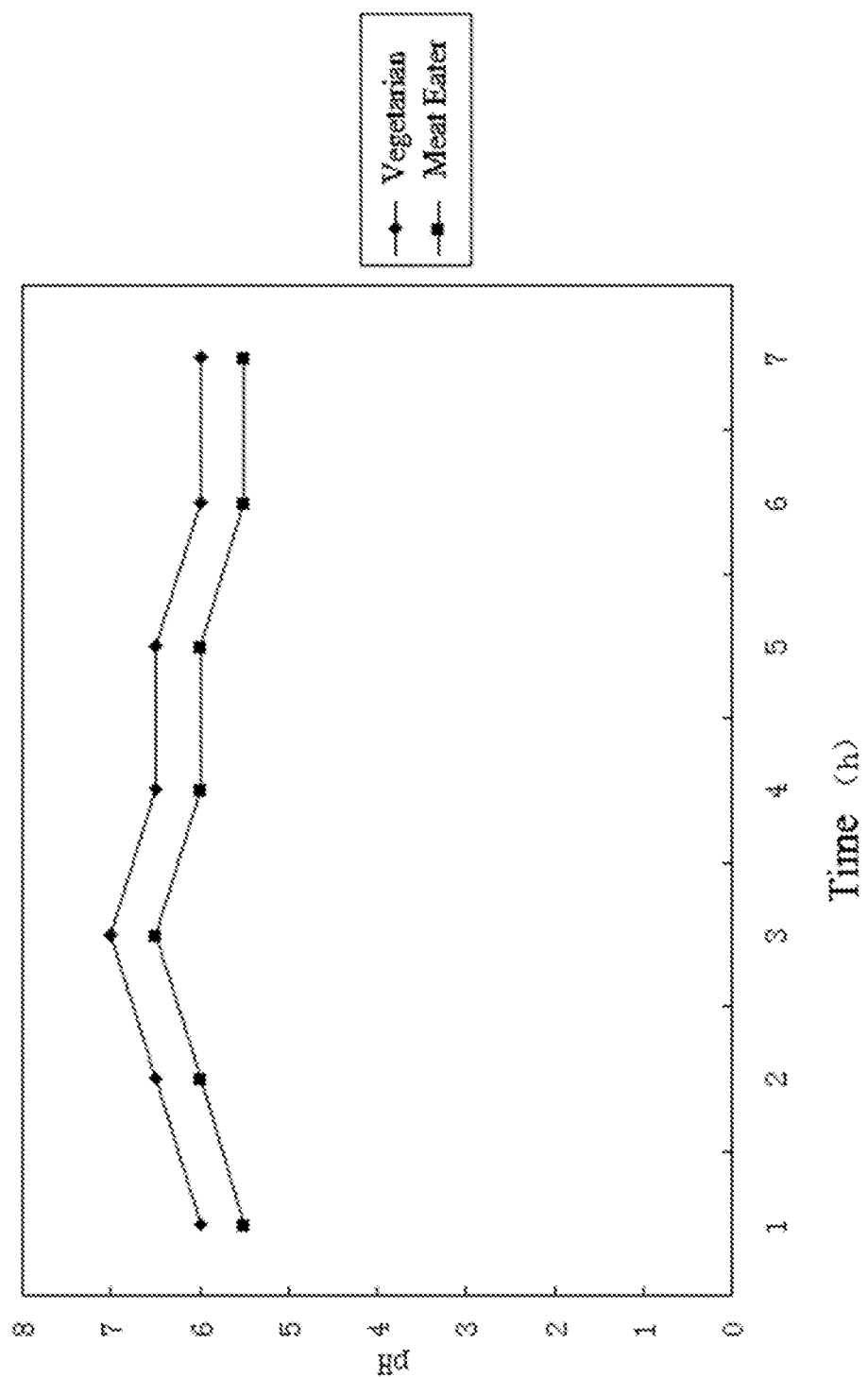

DRUG FOR KILLING ACID-FAST (RED) BACILLUS

CROSS REFERENCE OF RELATED APPLICATION

This is a national phase national application of an international patent application number PCT/CN2013/001393 with a filing date of Nov. 15, 2013, which claimed priority of two foreign applications which are filed in China: application number 201310011373.4 with a filing date of Jan. 11, 2013 and application number 201310177413.2 with a filing date of May 14, 2013. The contents of these specifications, including any intervening amendments thereto, are incorporated herein by reference.

BACKGROUND OF THE PRESENT INVENTION

Field of Invention

The present invention relates to medical technology, and more particularly related to using the raw materials for chemical testing or chemical engineering—basic fuchsine, as the key active ingredient and processing with traditional Chinese medicine and food article to manufacture a drug to cure tuberculosis and leprosy—a drug to kill acid-fast bacilli (red stain).

Description of Related Arts

Tuberculosis is a disease caused by *Mycobacterium tuberculosis*. *Mycobacterium tuberculosis* is a pathogen which causes infection inside the cell. *Mycobacterium tuberculosis* can adapt to acidic environment, is resistance against phagosomes of macrophages for a long period of time and can escape against the acidification of environment such that *Mycobacterium tuberculosis* can survive inside the body for an extended long period of time. Therefore, tuberculosis is a persistent and chronic infectious disease. *Mycobacterium tuberculosis* enters into the body from the respiratory tract, and through the blood stream, it spreads and bleeds in different organs, or even into the bone or lymph nodes. At present, the most common disease being caused is pulmonary tuberculosis, which is airborne and can be widely spread and impose great health hazards. Tuberculosis can be latent, carriers may have no obvious symptoms and therefore is hard to prevent. It is a big challenge and a long lasting health hazard to human.

Because of the emergence of resistant strains and the application of immunosuppression agents, the tuberculosis outbreak has worsen suddenly at worldwide level. According to WHO statistics, about one third of the world's population is infected by *M. tuberculosis*, and in some developing countries, the TB carriers in adults can reach 80% of which 5-8% TB carriers can develop into active TB disease.

At present, about eight million new cases of TB occur every year at worldwide level and causes the death of about three million people. In China, two hundred and fifty thousand people are died of TB every year, which is twice as the total number of death caused by transmissible diseases of all kinds. According, TB is a real worldwide health hazards to human.

*M. tuberculosis* enters into human body through the respiratory tract, survives and replicates inside the alveolar macrophages, then further spreads to proximal unactivated alveoli to form a Ghon focus. During the cell mediated immune response, *M. Tuberculosis* grows inside the macrophages and tubercles are formed of which the center of the tubercle is characterized by "caseation necrosis", that the tubercles are capable of restricting the multiplication of *M Tuberculosis*. For the majority of carriers of *M. tuberculosis*, the *M. tuberculosis* and its host are in a state of mutually coexistence, that the *M. tuberculosis* is surrounded by fiber inside the cheesy necrotic lesion and cannot undergo multiplication. However, when the human immune system is damaged and the human body is weakened, the restricted *M. tuberculosis* will be re-activated and replicate, a large number of *M. tuberculosis* will be released from the liquefied tubercles and spread throughout the human body. These patients with primary or secondary infection require drug treatment. The conventional first line drugs includes: 1. isoniazid, 2. rifampin, 3. streptomycin 4. pyrazinamide 5. ethambutol.

All these drugs have serious toxic side effect (For example, isoniazid and rifampin can easily cause elevated serum alanine aminotransferase, hepatomegaly, jaundice, nausea, vomiting, streptomycin can cause auditory nerve damage, ethambutol can caused optic nerve damage). In additional, during the treatment process, these drugs do not kill the bacteria and allow the bacteria to remain inside the body while only inhibiting its growth. The therapeutic effect is a negative result for sputum *Mycobacterium tuberculosis* (cannot detect acid-fast bacilli), that the bacteria is surrounded and hidden inside the human body. Once the body immune system is weak or is infected by an influenza, the bacteria will be activated and grow again, which is a painful process. The only treatment, again, is the drug treatment. Since the drug treatment may cause toxic side effect to the patients and causes damage to liver, kidney, nervous system, gastrointestinal and hematopoietic organ, the side effect may include extremely abnormal level of aspartate aminotransferase, alanine aminotransferase, urea, creatinine, urea nitrogen and etc. In some cases, hematuria may occur and the practitioner has to switch to liver and kidney treatment from TB treatment. Many TB patients cannot recover from TB but a great damage to liver and kidney is caused.

Leprosy:

*Mycobacterium leprae* is the pathogen which causes leprosy. The difference between this bacteria and other mycobacteria is that this bacteria cannot be cultured in artificial culture base. Therefore, the diagnosis of leprosy can only be relied on smear examination of acid-fast stain.

The common characteristics of *mycobacterium leprae* and *mycobacterium tuberculosis* are difficult to stain and resistance to decolorization by acid and alcohol after accepting a stain, therefore they are also referred to as acid-fast bacilli. Both of them do not have flagella, spore and capsule, and are Gram (G) positive bacilli (Red stain after acid-fast staining (+)).

In taxonomy, both *Mycobacterium leprae* and *Mycobacterium tuberculosis* are classified under the class Actinobacteria, the order Actinomycetales and the branch *Mycobacterium*. The differences between *Mycobacterium leprae* and *Mycobacterium tuberculosis* are summarized in Table 1:

TABLE 1

| Name | Infection Method | Growth Temp. | Infection site | In vitro cultivation | Transmission | Gram stain (G+) | Acid-Fast Stain |
|---|---|---|---|---|---|---|---|
| Mycobacterium tuberculosis | Inside phagocyte | 37° C. | Internal organs | Successful | Air | Positive | Positive (Red) |
| Mycobacterium leprae | Inside phagocyte | 28° C. | Body Surface (Skin) | Unsuccessful | Air Contacts | Positive | Positive (Red) |

At present, the drugs for *Mycobacterium leprae* are basically the same as the drugs for *Mycobacterium tuberculosis* except that the dosage for *Mycobacterium leprae* is much higher and the treatment course is longer. The commonly used drugs includes rifampin, chlorophenol diazoxide, sulfamide and etc., which are highly toxic drugs and may cause serious damage to liver, kidney, nervous system, gastrointestinal and hematopoietic organ.

Basic Fuchsine (also known as: new fuchsine, fuchsine salt, rosaniline hydrochloride):

1. Basic use of basic fuchsine

Basic fuchsine is the strongest nuclear stain which can stain particles of viscoelastic tissue and fuchsinophilic substances, and is a nuclear stain for central nervous system. In bacteriology, it is used to identify *Mycobacterium tuberculosis*. In analytical chemistry, it is used to prepare Schiff's reagent for aldehydes testing. In bromate titration, it is used as an redox indicator. It is also used for dyeing cotton, linen, artificial fibers, leather, feathers, fat and etc. as well as for manufacture of color precipitates.

2. Sources of Preparation

In the presence of iron and zinc chloride, react hydrochlorides of aniline, o-toluidine and p-toluidine with nitrobenzene for condensation, then separate by acid-base extraction and obtain by crystallization.

3. Chemical structure

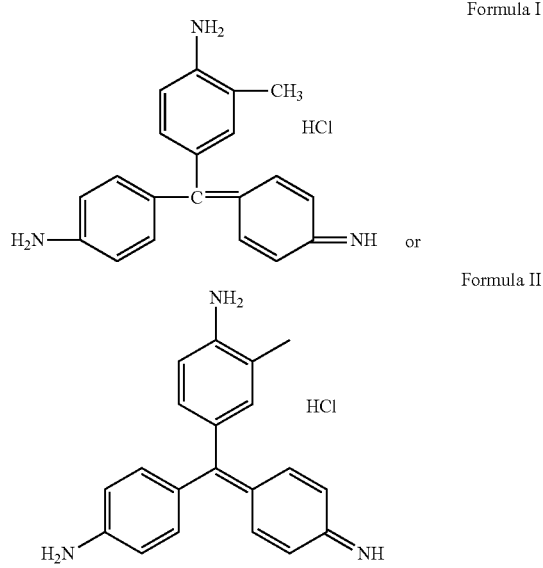

Formula I or

Formula II

Description of Structure:

For use as a stain for bacteria, the majority of synthetic substances are organic compounds containing a benzene ring (Basic fuchsine is one of the kind) in which a chromophore group and an auxochrome group are provided on the benzene ring. The chromophore group includes a nitro group (—NO2) and an azo group (—N═N—), while the auxochrome group includes a hydroxyl (—OH) and an amino group (—NH2). The chromophore group is responsible for the color of a compound and a benzene-containing compound with a chromophore group is called a chromogen. This type of compounds is not a dye because it does not have any affinity to the dying object and is easily separated from the dying object. Therefore, the auxochrome group is required. The auxochrome group does not contribute any color to the dyeing object but has the ability of dissociation to provide ionic character to a compound. After dissociation, the dye materials can bind to the dyeing object and provide color to the dyeing object.

The auxochrome group may be a basic group (such as a —NH2 group) or an acid group (such as a —OH group). The more the —NH2 group or the —OH group, the stronger is the basicity or acidity. If the number of each group is one, then the basic group will dominate. Accordingly, the pH of the dye can be determined by the nature of the auxochrome group. The basic fuchsine has no —OH group in its structure, and therefore is a basic dye.

Because organic dye is an organic acid or base with color which is difficult to dissolve in water and is soluble in organic solvent, usually they are made into salt in order to make them easier to dissolve in water. Therefore, basic fuchsine is also called fuchsine salt. In conclusion, the only difference between the above two formulae is just one auxochrome group ($CH_2$), which is a substance existed in the form of two structures in solution.

Principle of Acid-Fast Bacilli Stain

Acid-fast bacilli contains mycolic acid. Basic Fuchsine ($C_{20}H_{20}N_3Cl$ or $C_{19}H_{18}N_3Cl$) has a higher solubility in lipids than in hydrochloric acid and alcohol. Therefore, both can be combined strongly and is not easily decolorized by hydrochloric acid or alcohol. In addition, maintaining the integrity of the surface cell structure during the dyeing process is an important factor for maintaining its acid resistance. It is because a complete cell wall can prevent the overflow of lipids which is stained by basic fuchsine. Therefore, the red stain of the acid-fast bacilli can be maintained even after bleaching. Non acid-fast bacilli does not contain mycolic acid, cannot resist decoloring by hydrochloric acid or alcohol and therefore can be re-stained by methylene blue into blue color.

At present, the mechanism of bacteria stain is not completely clear. According to the available evidence, the dyeing process is neither purely physical nor purely chemical, but rather a combination of both.

According to the characteristics of acid-fast bacilli, acid-fast staining is mainly used in testing of *Mycobacterium tuberculosis* and *Mycobacterium leprae*.

4. Molecular formula and molecular weight $$C_{20}H_{20}N_3CL=337.84 \quad \text{Formula I:}$$

$$C_{19}H_{18}N_3CL=323.82 \quad \text{Formula II:}$$

5. Properties: green metallic luster crystal, soluble in ethanol and amyl alcohol, slightly soluble in water, red in color in aqueous solution, insoluble in ether.

SUMMARY OF THE PRESENT INVENTION

An object of the present invention is to provide a drug for killing acid-fast (Red stain) *bacillus*, that the drug can effectively killing acid-fast (Red stain) *bacillus*, completely eliminate the *Mycobacterium tuberculosis* and *Mycobacterium Leprae* inside human body and therefore is a cure for tuberculosis and leprosy.

In particular, the present invention provides a drug for killing acid-fast (Red stain) *bacillus*, characterized in that, the drug comprises basic fuchsine as the active ingredient.

According to the drug for killing acid-fast (Red stain) *bacillus* of the present invention, characterized in that, the drug comprises an excipient or an auxiliary ingredient which is pharmaceutically acceptable to the active ingredient basic fuchsine. Preferably, the excipient or the auxiliary ingredient is selected from ground rice, wheat germ or cereal. In particular, ground rice is mostly preferred. When ground rice is selected as the excipient, the drug composition by percentage weight is preferably: basic fuchsine 55-66%, ground rice 35-45%.

Nutrient content of ground rice: rich in fiber, great quantity of VB, VE vitamins and minerals such as calcium, phosphorus, iron and etc., commonly known as intestinal scavenger, improve gastrointestinal function, increase intestinal peristalsis, remove intestinal toxicity, timely discharge the intestinal garbage outside the body, provide relieve to constipation, promote absorption of nutrients, promote blood circulation, improve immunity, enhance physical fitness. Also, the dietary fiber which is rich in ground rice can combine to the cholesterol in the bile and promote the discharge of cholesterol, and provide cleansing effect to the blood and lipid regulation effect.

Wheat germ: concentrated source of several essential nutrients for life, including fat, protein, a variety of enzymes, vitamins, minerals and etc. The content of vitamin B1 is 3.5 times of our daily needs. Also contain a lot of vitamin E and linoleic fatty acid, and vitamin B6, which is not commonly found in other food.

According to the drug for killing acid-fast (Red stain) *bacillus* of the present invention, characterized in that, the drug is prepared into oral preparation, injectable preparation or external use preparation.

According to the drug for killing acid-fast (Red stain) *bacillus* of the present invention, characterized in that, the drug is prepared into tablets, oral solution, capsules, injection solution, ointments, tinctures, powders, granules, suppositories, creams, transdermal preparations or dietary supplements.

According to the present invention, the use of basic fuchsine for preparation of drug to inhibit or kill acid-fast (Red stain) *bacillus* and for the preparation of drug to treat tuberculosis and/or leprosy are provided.

The increase in pH in vivo is beneficial to removal of *Mycobacterium tuberculosis* and *Mycobacterium Leprae*:

The optimum pH of human body is between 7.35-7.45. This body condition has strongest immunity and highest enzymes activity level. The body fluids are weakly alkaline and is good for metabolism.

When the human body is infected by *M. Tuberculosis*, the pH of human body is decreased and the body becomes an acidic body (also called rancid body) because the bacteria's pH is between about 2-5 and hence the immunity is lowered. Since the pH value can directly affect the enzymatic activity of human body and hinder the immune response, while the composition of TB is complicated and its toxicity is related to the lipid content in the bacteria. For example, sulfolipids can inhibit the integration of lysosomes inside macrophage with phagosome. Accordingly, it is impossible to remove the bacteria from the human body.

When a patient object takes basic fuchsine, the pH of his body fluid (the urine being discharged) has a significantly increased trend. Therefore, the infected body, which is weakly acidic, is recovered to become weakly basic and this is beneficial to increasing the body's immunity such that *Mycobacterium tuberculosis* can be inhibited or removed. Because the integration of lysosomes inside macrophage with phagosome cannot be prevented, the bacteria can be removed. The changes in urine pH after taking basic fuchsine is illustrated in Table 2 and FIG. 1:

TABLE 2

Change of urine pH with time of Patient object (vegetarian)

| Time (h) | Patent's urine pH value | | | | | | | | | Average |
|---|---|---|---|---|---|---|---|---|---|---|
| | Li | Hu | Hou | Zhang | Qi | Hu | Yan | Wu | Cao | |
| Before drug | 5.5 | 6 | 6.5 | 6 | 5.5 | 6 | 6.5 | 6 | 6 | 6 |
| After drug 1 h | 6 | 6.5 | 7 | 6.5 | 6 | 6.5 | 7 | 6.5 | 6.5 | 6.5 |
| After drug 2 h | 6.5 | 7 | 7.5 | 7 | 6.5 | 7 | 7.5 | 7 | 7 | 7 |
| After drug 3 h | 6 | 6.5 | 7 | 6.5 | 6 | 6.5 | 7 | 6.5 | 6.5 | 6.5 |
| After drug 4 h | 6 | 6.5 | 7 | 6.5 | 6 | 6.5 | 7 | 6.5 | 6.5 | 6.5 |
| After drug 5 h | 5.5 | 6 | 6.5 | 6 | 5.5 | 6 | 6.5 | 6 | 6 | 6 |
| After drug 6 h | 5.5 | 6 | 6.5 | 6 | 5.5 | 6 | 6.5 | 6 | 6 | 6 |

Remarks: The urine pH value reached the peak value at 2-3 hours after taking drug, and the peak period can sustain for 3-4 hours, then return to normal at 5-6 hours after taking drug.

According to our studies, basic fuchsine can be used in preparation of drug for tuberculosis and leprosy. At present, we discovered that the use of basic fuchsine to treat tuberculosis is better than the existing treatment. The advantages are illustrated as follows:

(1) Not toxic: no liver or kidney damages is observed in patients taking drug for more than two years (2) Easily available and advantageous in promotion (3) Low cost, relieve financial burden to individual or nation (4) Thorough treatment: for patients who are recovered, no single occurrence of recurrence and all TB symptoms are disappeared.

(5) No adverse reactions: during the course of treatment, no side effect is observed in all cases (6) Treatment convenience: oral application is sufficient, no hospitalization is required.

(7) The drug will not remain inside the body while the body fluid can improve transiently. The change of urine pH after drug is illustrated in Table 2.

BRIEF DESCRIPTION OF THE DRAWINGS

FIG. 1 is the curve showing the changes of urine pH of patients with time after taking drug.

DETAILED DESCRIPTION OF THE PREFERRED EMBODIMENT

In this embodiment, the basic fuchsine is purchased from Tianjin Ju Hua Chemical Company Limited.

Embodiment 1

Toxicity Test of Basic Fuchsine

Materials: 24 white guinea pigs, purchased from Shenyang Pharmaceutical University, regular feeding; Basic fuchsine, from Tianjin Ju Hua Chemical Company Limited.

Matching and grouping of experimental animals: randomly divided into 4 groups (each group includes 6 counts, equal number of male and female), namely, control, high, medium, low fuchsine dosage group.

Method of administration: For each guinea pig, administered one time per day at a fixed time in the morning, the dosage for high, medium, low fuchsine dosage group are 8 mg/kg body weight/d, 6 mg/kg body weight/d, and 4 mg/kg body weight/d respectively; the drug administration period is 21 days, observe 3~4 times per day, observe the guinea pig by spirit condition, appetite, gloss level of skin and hairs, physical condition, alertness and ability to escape. No changes is observed after 21 days.

Embodiment 2

According to the principle of in vitro staining to *M. tuberculosis* and *M. leprae* (see acid-fast bacilli staining principle), it is learned that basic fuchsine has a special affinity to *M. tuberculosis* and *M. leprae* and is easily stained.

After taking basic fuchsine, the basic fuchsine activity over time can be observed through the blood phenomenon at different times. The fuchsine is absorbed into the bloodstream in a dissolved state, then through the process of blood cells, coloring or combination opportunity is provided to the *M. tuberculosis* and *M. leprae* inside the phagocytes, while the pH of body fluid is increased and the growing environment of the bacteria is destroyed, the bacteria is stained and the immune recognition ability is increased, then the activity of immune system is promoted to fully utilized. Accordingly, the basicity and the staining effect on bacteria of fuchsine are the key to remove or kill the bacteria.

Blood Observation

I. Observation object

1. Healthy individual as normal subject for observation
2. Patient recovered from the disease who volunteer to testing subject as volunteer subject II. Instrument:

Binocular microscope xsp-12G model

Manufacturer: Jiang Optical Instrument Main Factory

III. Reagents

Wright-Giemsa stain solution (available in the market)

Phosphate buffer (available in the market)

IV. Method of Operation

1. Obtain peripheral blood smear from normal subject and volunteer subject (normal control blood film, standby use)
2. Obtain peripheral blood smear from volunteer subject at different time after taking fuchsine (oral fuchsine blood film, standby use)
3. After the last blood sampling is complete, carrying staining together with the blood film before taking fuchsine orally of volunteer subject and the peripheral blood film of normal subject V. observe oral fuchsine blood film under microscope with 100× objective lens (oil immersion) and 12.5× eyepiece, real object is viewed under magnification at 1250 times and the results are shown in Table 3.

TABLE 3

Results of observation

| Drug taking time (h) | The status of Stain absorption by blood |
|---|---|
| 0.5 | Stain is cluster outside the cell in dissolved form, occasionally inside the cell, uneven distribution |
| 1 | Stain existed inside and outside the cell in dissolved form, such as in thick cloudy state, occurrence is more inside the cell than outside the cell |
| 2 | Uniform stain overflowed from the cell to outside is commonly seen, such as cloud mist state |
| 4 | Traces of stain is seen occasionally from the inside edge of cell |
| 6 | Just like the control normal blood film, no stain is observed |

Results of Observation:

1. After taking fuchsine, the fuchsine is absorbed through the body into the blood, then entered into the cell through the cell membrane, then remained inside the cell for about 2-4 hours.
2. The *Mycobacterium tuberculosis* and the *Mycobacterium Leprae* inside the phagocytes have the opportunities to combine to fuchsine, which is then stained or eliminated.

Embodiment 3

Drug Susceptibility Testing (I) Drug: Basic Fuchsine (II) Culture Method: Lowenstein-Jensen medium (Improved method)

(III) Composition of Lowenstein-Jensen medium:

$KH_2PO_4$: 2.4 g; $MgSO_4.7H_2O$ 0.24 g; magnesium citrate: 0.6 g; asparagine: 3.6 g; glycerin: 12 ml; distilled water: 600 ml; potato starch: 30 g; fresh whole egg liquid: 1000 ml; 2% malachite green solution: 20 ml (IV) Instrument 1. Digital Biochemical Incubator (Huangshi City Hengfeng Medical Devices Company Limited): 36° C. (special setting)
2. Biological safety cabinet: Biobase Bioteoh Model specifications: BSC-1500IZB2-X Manufacturer: Jinan Xinjiuxi Biotechnology Company Limited 3. Steam Incubator: 85° C.

Manufacturer: Beijing Xinzhongdaye Daibiao Company Limited

4. Drug: 2% basic fuchsine aqueous solution: 100 ml (V) Preparation of culture medium Add water to $KH_2PO_4$, $MgSO_4.7H_2O$, magnesium citrate, asparagine and glycerin, dissolve through heating in a boiling water bath, then add potato starch and continue heating in water bath for 30 minutes, stir continuously to form a uniform paste. After cooling to about 60° C., add 1000 ml fresh whole egg liquid and 20 ml 2% malachite green solution, mix thoroughly and then filter by double-layered gauze, then dispensed into test tube with screw cap. 7 ml of the prepared solution is added to each test tube, then add the 2% basic fuchsine solution according to a specific proportion into the test tube (see Table 3 for the adding amount), then place the test tube into the 85% steam incubator for 90 minutes, cooling to 60° C. or below and then place the test tube inclinedly into the biological safety cabinet (also called purification station), thereby the culture medium is cooled to solidify and form an incline surface. Put $10^{-2}$/ml living bacilli solution of *Mycobacterium tuberculosis* to the incline surface of the culture medium. The living bacilli solution for each tube is 0.1 ml. The concentration of bacilli solution in the culture medium is $10^{-3}$ mg/ml. Place in Digital Biochemical Incubator to culture. After culture for 5 weeks, no bacteria growth refers to drug susceptibility, continue bacteria growth refers to drug non-susceptibility (See Table 4 for testing results).

TABLE 4

| Testing results | | | | |
|---|---|---|---|---|
| Tube number | Adding amount of 2% basic fuchsine solution | Drug final dilution factor | Time in 36 C. incubator | Testing results |
| 1 | 0.7 ml | 500 | 5 weeks | Grow |
| 2 | 0.525 ml | 750 | 5 weeks | Grow |
| 3 | 0.35 ml | 1000 | 5 weeks | Grow |

Explanation of Drug Susceptibility Testing of Bacteria Growth:

Since basic fuchsine is non-toxic, in drug susceptibility testing, place basic fuchsine into the Lowenstein-Jensen medium will only cause the changes in color but no toxicity will be caused by the culture medium, and no nutrients content of the Lowenstein-Jensen medium will be affected. Also, since the medium does not provide a somatic environment, the bacteria should grow normally in this medium. This further proves that basic fuchsine is non-toxic, and that the fuchsine itself does not have a killing effect on the acid-fast bacilli killing effect. Instead, the basic fuchsine increases the pH of body fluid and stain the bacteria to become the target, thus the immunity system is activated to remove the bacteria thoroughly. This is the greatest advantage of this drug.

If standard drug is placed inside the Lowenstein-Jensen medium, this equals to giving toxic substances to the food of the bacteria, therefore the bacteria cannot grow because of food poisoning, therefore causing to the culture result as bacteria cannot grow (drug susceptibility). In other words, standard drugs can only have inhibition effect and fail to remove the bacteria thoroughly. Also, serious side effect may be resulted and damage to human detoxification is caused.

Important characteristics of using basic fuchsine to treat *Mycobacterium tuberculosis* and *Mycobacterium leprae* are summarized as follows:

1. Because basic fuchsine can increase pH of the body, causing the bacteria to lose its pH regulation effect, that unable to suppress phagocytes to secret plasmin, thus the fusion of lysosomes and phagosome will lead to the removal of bacteria.

2. Since basic fuchsine can stain the bacteria, while causing an increase in body pH, therefore the bacteria is tagged while the immunity is increased. Accordingly, the phagocytes is capable of identifying the target and has an increased engulfing ability to eliminate the bacteria.

3. Since basic fuchsine is intoxic, that its function mechanism is different from existing drug and it cannot inhibit or kill bacteria by toxicity effect, therefore during in vitro drug susceptibility, the bacteria cannot be killed and can growth normally in the culture medium due to the lack of somatic environment.

Embodiment 4

Basic Fuchsine for treatment of *Tuberculosis*

Dosage for patient: Capsule, 500 mg/capsule, where the weight ratio of basic fuchsine to ground rice is 3:2, each patient takes 1~2 capsule/day.

Method of administration: Every morning, before breakfast, take the capsule, three month as one treatment course, see Table 5 for patients' records, see Table 6 for treatment results.

Explanation for Patients' Records:

1. All patients were diagnosis and confirmed by standard TB hospital or TB prevention and treatment center, and all patients encountered disease recurrence after conventional standard drug treatment.

2. The patients, after conventional standard drug treatment, experienced liver and kidney damages of different level, and can no longer accept conventional standard drug.

3. Before drug treatment with basic fuchsine drug, all patients have obvious symptoms: body weakness, discomfort, fever, cough, night sweat, ascites, blood spitting, blood vomiting, etc. (skeletal TB patient experience pain, some experience amenorrhea).

4. Symptoms are significantly reduces after taking basic fuchsine for one month for majority of patients, TB symptoms are eliminated after taking basic fuchsine for three months, recovery are confirmed through X-ray after taking basic fuchsine for six months 5. Patients' blood test for liver and kidney after taking basic fuchsine shows that the blood test results are normal.

6. After taking basic fuchsine for one month, no *M. tuberculosis* is found in sputum (no acid-fast bacilli is found). After taking basic fuchsine for six month, the course of treatment is complete. Normal lives can be resumed physical labor activities can be done.

TABLE 5

| Patent Sex Age | Place of diagnosis | Name of disease | Sputum Acid-Fast Bacilli | Side Effect of Convention treatment | Disease Condition |
|---|---|---|---|---|---|
| Li XX F 65 | Shenyang Chest Hospital | Pulmonary TB | TB(+) | Dizziness, nausea, cannot eat, vomiting, very high uric acid test result, high transaminase test result | Cough, sputum with blood, whole body weakness, low-grade fever with increased seriousness in the afternoon, night sweat |
| Zhao XX F 38 | Jilin TB Hospital | Cavitary TB | TB(+) | Liver and kidney damage | Whole body weakness, fatigue, cough, low-grade fever, face flushing, night sweat, amenorrhea |
| Yu XX M 48 | Jilin TB Prevention and Treatment Center | Secondary TB | TB(+) | Nausea, vomiting, dizziness, liver and kidney damage, elevated transaminase and uric acid | Year round hands and foot fever, weakness, cough, night sweat, weight loss |
| Zhang XX F 62 | Liaoyuan City TB Hospital | Thoracic vertebrae TB | CT Scan TB(+) | Dizziness, nausea, liver and kidney damage, high transaminase | Relied on painkiller, cannot lie up and down by herself, sharp pain when coughing |
| Dong XX F 60 | Jilin TB Hospital | Infiltrate Pulmonary TB | TB(+) | Nausea, vomit, dizziness, fatigue, whole body weakness, high transaminase | fever with increased seriousness in the afternoon, night sweat, cough, whole body weakness, fatigue |
| Yu XX M 43 | Jilin TB Hospital | Pulmonary TB | TB(+) | Serious drug reaction, cannot eat, high transaminase and uric acid | Cough, fever, night sweat, weakness, fatigue, whole body discomfort, weight loss |
| Jiang XX M 26 | Shenyang Dongling Hospital | Pulmonary TB | TB(+) | Nausea, vomit, cannot eat, high transaminase and uric acid | Cough, fever, night sweat, weakness, fatigue, whole body discomfort |
| Wu XX M 21 | Jilin TB Hospital | Miliary TB | TB(+) | Nausea, vomit, dizziness, weight loss, high transaminase and uric acid | Cough, low-grade fever with increased seriousness in the afternoon, fact rash, night sweat, weakness |
| Yan XX F 22 | Shenyang Chest Hospital | Cavitary TB | TB(+) | No improvement after treatment (many times), liver and kidney damage, hydrothorax, significant lower back pain | Cough, night sweat, body weakness, aggregated flu, liver and kidney damage, weakness, menstruation amenorrhea |
| Wu XX F 63 | Heilongjiang Military Hospital | Neck and armpit lymph nodes TB | TB(+) | Insignificant treatment result with relief only, recurrence repeatedly, dizziness, vomit, nausea, weakness is aggravate | Serious cough, weakness, fatigue, enlarged neck and armpit lymph nodes, with hardening and pain |
| Yu XX F 69 | Siping TB Hospital | Pulmonary TB | TB(+) | Nausea, vomiting, dizziness, liver and kidney damage | Cough, sputum production, occasional low-grade fever, weakness, fatigue |

TABLE 5-continued

Patients' records of TB Patients

| Patent Sex Age | Place of diagnosis | Name of disease | Sputum Acid-Fast Bacilli | Side Effect of Convention treatment | Disease Condition |
|---|---|---|---|---|---|
| Sun XX M 32 | Siping TB Hospital | Cavitary TB | TB(+) | dizziness Nausea, liver and kidney damage, weakness, night sweat | Cough, low-grade fever, weakness, fatigue, weight loss |
| Hou XX M 60 | Siping TB Hospital | Pulmonary TB | TB(+) | Nausea, anorexia, increased heartbeat, weakness, high transaminase | Low-grade fever, night sweat, whole body weakness, cough |
| Qi XX F 62 | Shenyang No. 2 TB Hospital | Pulmonary TB | TB(+) | Nausea, dizziness, liver and kidney damage | Cough, low-grade fever, weakness, fatigue |
| Meng XX M 51 | Shenyang Dongling TB Hospital | Pulmonary TB | TB(+) | Nausea, anorexia, liver and kidney damage, elevated transaminase | Cough, easy to get a flu, night sweat, fatigue, weakness |
| Zhou XX F 77 | Fushun TB Hospital | Pulmonary TB | TB(+) | Nausea, increased heartbeat, liver and kidney damage | Cough, weakness, fatigue, drowsiness, easy to catch a cold |
| Li XX F 49 | Fushun TB Hospital | Pulmonary TB | TB(+) | Headache, anorexia, liver and lung damage, high transaminase | Cough, sputum production, weakness, night sweat, fatigue, whole body discomfort |
| Li XX M 48 | Fushun TB Hospital | Tuberculosis Pleurisy | TB(+) | Nausea, headache, anorexia, liver and kidney damage, terminated treatment, thoracentesis 4 times | Weak, fatigue, discomfort, low-grade fever, night sweat, chest pain, cough |
| Zhang XX F 26 | Zhangchun TB Hospital | Double Miliary TB | TB(+) | Whole body weakness, nausea, anorexia, dizziness, liver and kidney damage | Cough, low fever, more serious in the afternoon, night sweat |
| Wamg XX M 40 | Jilin Jiutai TB Hospital | Double Miliary TB, 3 cavity in the lung | TB(+) | Nausea, anorexia, headache, liver and kidney damage | Cough, blooding spitting, whole body weakness, low-grade fever, night sweat, bedrest, weight loss |

TABLE 6

Treatment results of TB Patients

| Patent Sex Age | Dosage (capsule/day) | Drug treatment after 1 month | Drug treatment after 3 month | Drug treatment after 6 month |
|---|---|---|---|---|
| Li XX F 65 | 1 | TB Improved (−) | Resume physical strength, TB symptoms such as fatigue are eliminated | TB (−) confirmed by X-ray, liver and kidney function normal |
| Zhao XX F 38 | 1 | TB Improved (−) normal menstruation | Symptoms of night sweat, cough, weakness low-grade fever are eliminated | TB (−) confirmed by X-ray, liver and kidney function normal |

TABLE 6-continued

Treatment results of TB Patients

| Patent Sex Age | Dosage (capsule/day) | Drug treatment after 1 month | Drug treatment after 3 month | Drug treatment after 6 month |
|---|---|---|---|---|
| Yu XX M 48 | 1 | TB Improved (−) | Resume physical strength, symptoms of cough night sweat and low-grade fever are eliminated | TB (−) confirmed by X-ray, liver and kidney function normal |
| Zhang XX F 62 | 2 | Pain reduced | Resume physical strength, pain is relieved, stop use of painkiller | liver and kidney function normal, no significant changes in X-ray |
| Dong XX F 60 | 1 | Reduced symptoms of cough and others | Resume physical strength, TB symptoms are eliminated | TB (−) confirmed by X-ray, liver and kidney function normal |
| Yu XX M 43 | 1 | Cough and night sweat disappeared, Improved | Resume physical strength, symptoms of cough, weakness and night sweat are eliminated | TB (−) confirmed by X-ray, liver and kidney function normal |
| Jiang XX M 26 | 1 | Normal transaminase TB (−) | All TB symptoms are eliminated | TB (−) confirmed by X-ray, liver and kidney function normal |
| Wu XX M 21 | 1 | Normal transaminase TB (−) | All TB symptoms are eliminated, physical strength is improved | TB (−) confirmed by X-ray, liver and kidney function normal |
| Yan XX F 22 | 1 | No lower back pain, normal menstruation, TB (−) | All TB symptoms are eliminated, physical strength is improved, ascites dissappeared | TB (−) confirmed by X-ray, liver and kidney function normal |
| Wu XX F 63 | 1 | Improved, softening of hard tissue | Resume physical strength, all TB symptoms are eliminated | TB (−), neck and armpit tubercles disappeared |
| Yu XX F 69 | 1 | Improved TB (−) | Feel body strength, cough is gone, not fatigue anymore, low-grade fever disappaeared | TB (−) confirmed by X-ray, liver and kidney function normal |
| Sun XX M 32 | 1 | Significantly improved TB (−) | Resume physical strength, weight gain, all TB symptoms are eliminated | TB (−) confirmed by X-ray, liver and kidney function normal |
| Hou XX M 60 | 1 | Improved TB (−) | Fatigue is gone, feel to have strength, all all TB symptoms are eliminated | TB (−) confirmed by X-ray, liver and kidney function normal |
| Qi XX F 62 | 1 | Improved TB (−) | Resume physical strength, not fatigue anymore, all TB symptoms are eliminated | TB (−) confirmed by X-ray, liver and kidney function normal |
| Meng XX M 51 | 1 | Improved TB (−) | Cough disappeared, whole body with strength again, all TB symptoms are eliminated | TB (−) confirmed by X-ray, liver and kidney function normal |
| Zhou XX F 77 | 1 | Improved TB (−) | fatigue disappeared, cough is gone, all TB symptoms are eliminated | TB (−) confirmed by X-ray, liver and kidney function normal |
| Li XX F 49 | 1 | Improved TB (−) | Feel improved physical strength, fatigue and all TB symptoms are eliminated | TB (−) confirmed by X-ray, liver and kidney function normal |
| Li XX M 48 | 1 | Significantly improved TB (−) | improved physical strength, all TB symptoms are eliminated, ascites disappeared | TB (−) confirmed by X-ray, liver and kidney function normal |
| Zhang XX F 26 | 1 | Improved TB (−) | Cough and all TB symptoms are eliminated | TB (−) confirmed by X-ray, liver and kidney function normal |

TABLE 6-continued

Treatment results of TB Patients

| Patent Sex Age | Dosage (capsule/ day) | Drug treatment after 1 month | Drug treatment after 3 month | Drug treatment after 6 month |
|---|---|---|---|---|
| Wang XX M 40 | 1 | Improved TB (−) | all TB symptoms are eliminated, feel improved physical strength, weight gain | TB (−) confirmed by X-ray, liver and kidney function normal |

Embodiment 5

Basic Fuchsine for Treatment of Leprosy:
I. Type of drug:
1. Oral capsule: Dosage for patient: Capsule, 500 mg/capsule, where the weight ratio of basic fuchsine to ground rice is 3:2, each patient takes 1~2 capsule/day;
2. Topical tincture, apply to ulcer surface.
II. Preparation of Basic Fuchsine Tincture:
Materials: 1. Basic fuchsine, 2. Medical alcohol (75% ethanol solution)
Preparation Process:
1. Pour 100 g basic fuchsine and 800 ml 75% ethanol into a glass beaker, then stir evenly by a glass rod.
2. Grip an alcohol cotton with forceps, light up by a lighter and place to the surface of the beaker which contains basic fuchsine and 75% ethanol, ignite the mixture, stir with the glass rod while burning until the flame is out.
3. Wait till the temperature reached 60° C., then pour the drug solution after burning into a grinding jar through a funnel.
4. Soaking the prepared tincture solution into cotton ball in an auxiliary tank.
III. Method of Use
External use: wash the ulcer surface of leprosy patients with saline, then apply the cotton ball which is prepared with basic fuchsine tincture solution, apply repeatedly and then wrap by gauze. Repeat the above steps every 3 days until the wound is healed.
Internal use: Every morning before breakfast, take 1 capsule with warm water until recovery. One treatment course is three months. See Table 7 for treatment results.
Explanation for patients' records: The subjects are patients from Shandong Tengzhou City Leprosy Village and patients from Leprosy Rehabilitation Center of Puguang Hospital in Wuchaun City, Guangdong Province.

TABLE 7

Patient's records of Leprosy Patients

| Patent Sex Age | Name of disease | Years of Ulcer | Convention treatment method | Condition before Fuchsine Treatment | Treatment method | Treatment results | Remarks |
|---|---|---|---|---|---|---|---|
| Du XX M 81 | Leprosy ulcers | More than 60 years | Serious drug reaction, increased ulcer area, bone pain | Cannot sleep due to pain, swollen and red calf | Oral and external | After oral treatment for 7 days, leg's swelling and redness disappeared, ulcer area is reduced | After treatment for 1 month, scab is formed on the ulcer area |
| Zhang XX M 68 | Leprosy ulcers | More than 40 years | Palpitation, nausea, anorexia | Swollen and red finger, sticky, ulcer on feet | Oral and external | After oral treatment for 10 days, swelling and redness disappeared, foot ulcer area is reduced | After treatment for 1 month, scab is formed on the ulcer area, hands are healed |
| Cao XX M 76 | Leprosy ulcers | Few decades | Used many external medication but ineffective | Ulcer and bleeding on two feet | External | After half month, area of ulcer is reduced, scab is formed at the edges | Absorbed, continue treatment |
| Liu XX M 70 | Leprosy ulcers | Many years | Used many external medication but ineffective | Ulcer on one foot | External use of tincture | scab formed after half month | Continuous monitoring |

TABLE 7-continued

Patient's records of Leprosy Patients

| Patent Sex Age | Name of disease | Years of Ulcer | Convention treatment method | Condition before Fuchsine Treatment | Treatment method | Treatment results | Remarks |
|---|---|---|---|---|---|---|---|
| Chen XX M 66 | Leprosy ulcers | 45 years | Used many external medication but ineffective | Pus and pain on one foot | External use of tincture | scab formed after half month | Pain disappeared on the day of application |

One skilled in the art will understand that the embodiment of the present invention as shown in the drawings and described above is exemplary only and not intended to be limiting. It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An oral drug preparation for killing acid-fast *bacillus* having a drug composition by percentage weight of basic fuchsine 55-66% and ground rice 35-45%, wherein the basic fuchsine is an active ingredient to kill the acid-fast *bacillus* and the ground rice is an excipient or an auxiliary ingredient.

2. The oral drug preparation for killing acid-fast *bacillus* according to claim 1, characterized in that: the oral drug preparation is a tablet, capsule, powder, granule, or dietary supplement.

* * * * *